US009962523B2

(12) United States Patent
Lampropoulos et al.

(10) Patent No.: US 9,962,523 B2
(45) Date of Patent: May 8, 2018

(54) CATHETER WITH RADIOPAQUE MARKER

(75) Inventors: Fred P. Lampropoulos, Salt Lake City, UT (US); Nicholas Gerald Accisano, III, Howell, NJ (US)

(73) Assignee: Merit Medical Systems, Inc., South Jordan, UT (US)

(*) Notice: Subject to any disclaimer, the term of this patent is extended or adjusted under 35 U.S.C. 154(b) by 1465 days.

(21) Appl. No.: 12/147,933

(22) Filed: Jun. 27, 2008

(65) Prior Publication Data

US 2009/0326560 A1 Dec. 31, 2009

(51) Int. Cl.
*A61M 25/01* (2006.01)
*A61M 25/00* (2006.01)

(52) U.S. Cl.
CPC .... *A61M 25/0108* (2013.01); *A61M 25/0009* (2013.01); *A61M 25/007* (2013.01); *A61M 2025/0096* (2013.01); *A61M 2025/0163* (2013.01)

(58) Field of Classification Search
CPC ............ A61M 25/007; A61M 25/0108; A61M 25/0009; A61M 2025/0163; A61M 2025/0096; A61M 2025/0286; A61M 27/00; A61M 2027/004; A61M 1/008; A61M 1/0023
USPC ......... 427/2.1; 604/100.01, 103.1, 524, 529; 606/148
See application file for complete search history.

(56) References Cited

U.S. PATENT DOCUMENTS

| | | | |
|---|---|---|---|
| 2,212,334 A * | 8/1940 | Wallerich | ...................... 264/330 |
| 2,481,964 A | 9/1949 | Wollan | |
| 3,181,926 A | 5/1965 | Busche | |
| 3,314,430 A | 4/1967 | Alley et al. | |
| 3,788,328 A | 1/1974 | Alley et al. | |
| 4,199,623 A | 4/1980 | Nuzzi et al. | |
| 4,419,095 A * | 12/1983 | Nebergall | ......... A61M 25/0108 128/207.15 |
| 4,516,970 A | 5/1985 | Kaufman et al. | |
| 4,657,024 A * | 4/1987 | Coneys | ........................ 600/435 |
| 4,681,110 A | 7/1987 | Wiktor | |

(Continued)

FOREIGN PATENT DOCUMENTS

| | | | |
|---|---|---|---|
| DE | 19635951 | | 9/1996 |
| EP | 0987042 | * | 3/2000 |

(Continued)

OTHER PUBLICATIONS

Notification of Transmittal of the International Search Report and the Written Opinion of the International Searching Authority dated Jun. 8, 2009 in International Application No. PCT/US2009/040355.

(Continued)

*Primary Examiner* — Bhisma Mehta
*Assistant Examiner* — Brandy S Lee
(74) *Attorney, Agent, or Firm* — Stoel Rives LLP (57) ABSTRACT

A catheter having a radiopaque marker. The radiopaque marker is disposed on a distal end of the catheter tube and is configured to allow for simple and efficient identification of the location of a predetermined drainage bore on an X-ray or other radiographic technique. In one implementation, the radiopaque marker is associated with the catheter tube such that inclusion of the radiopaque marker does not increase the outer diameter or decrease the inner diameter of the tube.

19 Claims, 7 Drawing Sheets

(56) References Cited

U.S. PATENT DOCUMENTS

| | | | |
|---|---|---|---|
| 5,019,886 A | 5/1991 | Sato et al. | |
| 5,045,071 A | 9/1991 | McCormick et al. | |
| 5,084,022 A | 1/1992 | Claude | |
| 5,114,401 A | 5/1992 | Stuart et al. | |
| 5,116,652 A | 5/1992 | Alzner | |
| 5,156,979 A | 10/1992 | Sato et al. | |
| 5,203,777 A * | 4/1993 | Lee | 604/529 |
| 5,217,440 A | 6/1993 | Frassica | |
| 5,253,653 A | 10/1993 | Daigle et al. | |
| 5,267,574 A | 12/1993 | Viera et al. | |
| 5,300,048 A | 4/1994 | Drewes, Jr. et al. | |
| 5,416,822 A | 5/1995 | Kunik | |
| 5,558,652 A * | 9/1996 | Henke | 604/529 |
| 5,707,879 A | 1/1998 | Reinitz | |
| 5,735,829 A * | 4/1998 | Cherian | A61M 25/007 604/174 |
| 5,820,918 A | 10/1998 | Ronan et al. | |
| 5,858,556 A | 1/1999 | Eckert et al. | |
| 5,948,489 A | 9/1999 | Hopkins | |
| 6,036,682 A * | 3/2000 | Lange et al. | 604/529 |
| 6,261,260 B1 | 7/2001 | Maki et al. | |
| 6,277,108 B1 | 8/2001 | McBroom et al. | |
| 6,375,660 B1 | 4/2002 | Fischell et al. | |
| 6,388,260 B1 | 5/2002 | Doty et al. | |
| 6,540,721 B1 * | 4/2003 | Voyles | A61B 17/22 604/103.1 |
| 6,623,823 B1 | 9/2003 | Onwumere | |
| 6,635,082 B1 | 10/2003 | Hossainy et al. | |
| 6,638,245 B2 * | 10/2003 | Miller et al. | 604/96.01 |
| 6,727,504 B1 | 4/2004 | Doty | |
| 7,077,837 B2 | 7/2006 | Sahagian | |
| 8,394,448 B2 | 3/2013 | Lachner | |
| 2001/0025937 A1 | 10/2001 | Imai | |
| 2002/0190559 A1 | 12/2002 | Phillips et al. | |
| 2002/0198559 A1 | 12/2002 | Mistry et al. | |
| 2003/0023190 A1 | 1/2003 | Cox | |
| 2003/0167052 A1 | 9/2003 | Lee et al. | |
| 2004/0084626 A1 | 5/2004 | McGregor | |
| 2004/0099810 A1 | 5/2004 | Gerstenmayer | |
| 2004/0104500 A1 | 6/2004 | Bross et al. | |
| 2005/0004649 A1 | 1/2005 | Mistry et al. | |
| 2005/0006757 A1 | 1/2005 | Rinella et al. | |
| 2005/0064223 A1 * | 3/2005 | Bavaro | A61B 5/1076 428/615 |
| 2005/0064224 A1 | 3/2005 | Bavaro et al. | |
| 2005/0065434 A1 | 3/2005 | Barao et al. | |
| 2005/0283226 A1 | 12/2005 | Haverkost | |
| 2006/0201601 A1 | 9/2006 | Furst et al. | |
| 2006/0210700 A1 * | 9/2006 | Lachner | 427/2.1 |
| 2007/0242802 A1 | 10/2007 | Dafni | |
| 2008/0097394 A1 * | 4/2008 | Lampropoulos et al. | 604/524 |
| 2009/0318895 A1 | 12/2009 | Lachner | |
| 2009/0326560 A1 | 12/2009 | Lampropoulos et al. | |

FOREIGN PATENT DOCUMENTS

| | | |
|---|---|---|
| EP | 987042 | 3/2000 |
| JP | 101304 | 1/1998 |
| WO | 2002067014 | 8/2002 |

OTHER PUBLICATIONS

Restriction Requirement dated Jun. 1, 2007 in co-pending U.S. Appl. No. 11/083,842.
Response to Restriction Requirement filed Aug. 30, 2007 in co-pending U.S. Appl. No. 11/083,842.
Office Action dated Nov. 19, 2007 in co-pending U.S. Appl. No. 11/083,842.
Amendment and Response filed May 19, 2008 in co-pending U.S. Appl. No. 11/083,842.
Office Action dated Sep. 17, 2008 in co-pending U.S. Appl. No. 11/083,842.
Interview Summary dated Dec. 15, 2008 in co-pending U.S. Appl. No. 11/083,842.
Amendment and Response filed Mar. 17, 2009 in co-pending U.S. Appl. No. 11/083,842.
Notice of Non-Compliant Amendment dated Jul. 2, 2009 in co-pending U.S. Appl. No. 11/083,842.
Notice of Abandonment dated Jan. 27, 2010 in co-pending U.S. Appl. No. 11/083,842.
European Search Report dated Aug. 19, 2011 for EP09770595.8 (PCT/US2009/040355).
Office Action dated Aug. 22, 2011 for U.S. Appl. No. 12/549,241.
Office Action dated Mar. 20, 2012 for U.S. Appl. No. 12/549,241.
Notice of Allowance dated Sep. 17, 2012 for U.S. Appl. No. 12/549,241.
Office Action dated Jun. 6, 2011 for U.S. Appl. No. 11/883,842.
Bell, et al., Neutron Detection with Cyrogenics and Semiconductors, 2005, 1592-1605.
Gao, et al., Preparation of Nanostructured Hexagonal Boron Nitride Powder, 2003., 1982-1984.
McGregor, et al., Design considerations for Thin Film Coated Semiconductor Thermal Neutron Detectors—I: Basics Regarding Alpha Particle Emitting Neutron Reactive Films, 2003, 272-308.
McGregor, et al., Spectral Identification of Thin-Film-Coated and Solid-Form Semiconductor Neutron Detectors, 2004, 180-188.
Schmid, et al., A Neutron Sensor Based on Single Crystal CVD Diamond, 2004, 554-561.

* cited by examiner

CATHETER WITH RADIOPAQUE MARKER

BACKGROUND OF THE INVENTION

Field of the Invention

The present disclosure relates to catheters. In more particular, the present invention relates to a catheter having a radiopaque marker adapted to allow a practitioner to simply and efficiently identify the precise location of a predetermined drainage bore located on a catheter that is positioned within a patient.

Relevant Technology

One of the important therapeutic tools in modern medicine relates to the removal of volumes of fluids from a predetermined location within a patient's body. Fluids that collect in a patient's tissue, body cavities, or other positions within the patient's body, and which exceed normal volumes can contribute to infection, exert potentially harmful pressure on the patient's organs, or otherwise impede in the proper care and recovery of a patient. Drainage catheters have long been utilized to drain such excess volumes of fluids from a patient's body. Typically, the drainage catheter is adapted to be introduced into the patient at the site where the excess fluid is accumulated. A plurality of drainage bores are positioned in a distal end of the catheter to allow the passage of the fluids and any materials suspended in the fluids from the volume of fluid to the lumen of the catheter.

The distal end of drainage catheters are typically adapted to form an anchor configuration to secure the drainage catheter at the site where excess fluid is accumulated. However, the tissue surrounding drainage sites often does not provide a solid or reliable substrate to maintain the position of the catheter within the patient. As a result, the anchor configuration of the catheter is typically formed in a relatively large pigtail type loop that provides a reliable anchor regardless of the characteristics of the surrounding tissue. The pigtail loop is formed by securing the tip of the catheter tube such that the tip of the catheter contacts a more proximal position on the catheter tube. This is accomplished by utilizing a suture that is threaded between the proximal position and the tip of the catheter. The suture is adapted to run the length of the catheter and exit the catheter at the proximal end of the catheter tube. This allows the user to manipulate the suture to maintain or release the anchor configuration of the distal end of the catheter while the distal end of the catheter is positioned inside the patient.

A problem associated with inserting and properly anchoring a drainage catheter within a patient relates to identifying the disposition of the bore holes within a patient and determining that the catheter has been advanced to the desired location within the patient such that it can be anchored within a target cavity or tissue within the patient. A practitioner will typically advance the drainage portion of the catheter until all bore holes of the catheter are disposed within the cavity to be drained of fluid. This avoids accidental drainage of fluid out of one body cavity or locale within the patient and into another cavity or tissue, rather than being drained from the cavity to outside the patient.

Traditionally, radiopaque markers have been used in conjunction with X-ray radiography to determine the location of a distal end of a catheter within the patient. Radiographic techniques utilize imaging techniques to visualize internal patient structures and/or objects within a patient. The term "imaging techniques" is generically used. Examples of imaging techniques include X-ray radiography to identify both the technique of projection radiography using X-ray radiation and the resulting image, which may be on film or captured digitally and viewed via an electronic medium. Other radiographic techniques include Fluorography and Computed Tomography scan (CT or CAT scan). Additional imaging techniques subsumed within the term do not use X-rays but may still be useful for identifying the position of a catheter with a radiopaque marker within a patient. Such techniques may include ultrasound, and Magnetic Resonance Imaging (MRI), although MRI may be contraindicated for use with some types of radiopaque markers.

Conventionally, radiopaque markers are metallic pieces disposed at a given position on a drainage catheter to allow a practitioner to identify the position of the catheter within the patient. As their name implies, radiopaque markers at least partially block X-rays and so that the marker can be clearly distinguished via radiography from patient tissues surrounding the marker. This allows for ready appreciation of the approximate location of the bore holes within the patient.

There are a number of deficiencies of the traditional metal bands comprising typical radiopaque markers. Such metal bands may become loosened from the catheter tube such that they can rotate around the tube or even possibly slide up and down the tube. The possibility of the marker band being displaced from its predetermined position is a significant problem with traditional bands. Movement of a marker band can be particularly problematic to the extent that the location of the distal end of the catheter tube may no longer be indicated by the maker. An additional problem relates to the fact that it is difficult to align the metal bands with drainage bores of the catheter. For example, punching holes through both the metal radiopaque marker band and the elastomeric catheter can result in damage to one or both of the radiopaque marker band and the catheter. This is due to the hardness of the marker band and the softness of the catheter tube.

Attempts to align preformed drainage bores in the marker band and the catheter tube can be difficult or impractical. Additionally, inadvertent rotation of the band around the tube may cause a bore hole present in the band to become misaligned with a bore hole in the tube, thereby reducing the ability of the catheter to drain fluid. As a result, marker bands are positioned either distally or proximally with relation to the drainage apertures. However, slipping of the marker band can lead to miscalculations of the orientation of the marker bands to the drainage apertures. In some circumstances, the marker band can even inadvertently obstruct a drainage bore of the catheter. Even where the marker band does not slip, the practitioner is required to make estimations of the actual location of a particular drainage bore relative to the marker band.

Another difficulty relates to the fact that inclusion of the marker band on the catheter tube can increase the outer diameter of the catheter tube or require special processing to minimize any increase in the diameter of the catheter tube. In some cases, an undesirable ridge or other profile is created which can interfere with normal operation of the catheter. A variety of complicated assembly techniques have been developed to secure marker bands between multiple wall layers of catheter tubes. These techniques can require complex machinery, assembly and cost. Additionally, such techniques do not lend themselves to the positioning of a drainage bore contiguous with the marker band.

BRIEF SUMMARY OF THE INVENTION

The present invention relates to catheters. In more particular, the present invention relates to a drainage catheter having a radiopaque marker band. The radiopaque marker band is disposed on the distal end of the catheter and allows quick, simple and reliable identification of a precise location of one or more bores of the catheter using on an X-ray or other imaging technique. For example, the marker may be disposed at the last drainage bore. For example, according to one implementation, the radiopaque marker band can be positioned such that it corresponds to the first drainage bore, or in other words, the bore positioned proximal to the other drainage bores formed within the catheter tube. According to one aspect of the present invention, the radiopaque marker band is adapted such that it does not increase an outer diameter or decrease an inner diameter of the tube at, or adjacent to, the location of the marker band.

According to one aspect of the present invention, a practitioner positions the distal end of the catheter tube in a desired position within a patient's body, such as a volume of bodily fluid to be drained. The distal end of the catheter is inserted into the patient's body in a straightened or linear configuration. Once an initial position of the distal end of the catheter is achieved, X-ray or some other type of radiography may be performed to determine that the catheter is positioned within a desired position within the patient. The radiopaque marker is fixedly located at a predetermined position relative to a proximal, or first, bore. Due to the position of the radiopaque marker at the first bore, the practitioner can readily ascertain whether each of the bores is positioned in the volume of fluid or other desired position within the patient.

If the initial position of the distal end of the catheter is not acceptable, the distal end can be re-positioned until a desired position is achieved and confirmed using radiography. Once a desired position is achieved, the catheter can be secured in place to maintain the position of the catheter within the patient's body. This is often accomplished by tensioning a suture, which draws a distal tip of the tube until it contacts a more proximal portion of the tube, thereby forming a pigtail loop. Alternatively, the initial position may be secured and a radiograph performed at a later time. In yet another embodiment, the position may be determined using real-time radiography, such as fluoroscopy.

According to one aspect of the present invention, the radiopaque marker comprises a band of polyurethane material that is impregnated with, or otherwise comprises, one or more radiopaque materials, such as metal, metal flakes, metal powder, ceramics, ceramics powder, Barium Sulfate ($BaSO_4$), Bismuth Subcarbonate ($Bi_2O_2(CO_3)$), Bismuth Trioxide ($Bi_2O_3$) or any other suitable radiopaque material, or a mixture of any of the above materials. The radiopaque marker band is configured to be integrated into the catheter tube body in a simple and straightforward construction. Additionally, the integration of the radiopaque material does not result in the interposition of an additional catheter layer over the radiopaque material. According to one aspect of the present invention, the radiopaque material marker band is slid over an end of the catheter tube, positioned at a predetermined location, and then heat fused to the catheter tube. During heat fusion, a mandrel or plug is positioned on the inside of the tube and a confinement tube is positioned on the outside of the tube such that neither the inside or outside diameter of the tube is altered during or after the heat fusion process.

After heat fusion, the mandrel and confinement tube are removed. The drainage bore holes are then formed in the distal end of the catheter tube. A first drainage bore, which is configured to be the proximal most drainage bore along the length of the catheter, is formed in the radiopaque marker band. According to one aspect of the present invention, the drainage bore is approximately centered within the band of radiopaque material to give the practitioner a precise location of the drainage bore when the drainage catheter is positioned within the patient's body. The metal that comprises the radiopaque material may comprise platinum, gold, tungsten, lead, other radiopaque materials, or a mixture of radiopaque materials.

As will be appreciated by those skilled in the art, a variety of types and configurations of radiopaque markers can be utilized without departing from the scope and spirit of the present invention. For example, the first, or proximal-most bore may be disposed proximally or distally relative to the marker. Alternatively, the proximal-most bore may be positioned within the marker band but not centered on the marker band. The drainage bores may be formed in the distal end portion, the marker band, or both the distal end and the marker band prior to heat fusion of the marker to the tube.

According to one embodiment, the marker band comprises strips of radiopaque material aligned with the longitudinal axis of the catheter tube. According to another embodiment, the marker material may define a band of material that comprises a clip, wherein prior to heat fusion, the band is temporarily attached to the catheter tube portions via the clip. According to yet another embodiment, the catheter can include a recessed area which accommodates the marker band prior to heat fusion. According to yet further embodiments, the marker band may be secured utilizing a variety of methods including radio-frequency (RF) welding, heat fusion using forced hot air, a quartz heating lamp, or any other suitable concentrated and/or localized heat source. These and other objects and features of the present invention will become more fully apparent from the following description and appended claims, or may be learned by the practice of the invention as set forth.

BRIEF DESCRIPTION OF THE DRAWINGS

The present embodiments will become more fully apparent from the following description and appended claims, taken in conjunction with the accompanying drawings. Understanding that the accompanying drawings depict only typical embodiments, and are, therefore, not to be considered to be limiting of the invention's scope, the embodiments will be described and explained with specificity and detail in reference to the accompanying drawings in which:

DETAILED DESCRIPTION OF THE PREFERRED EMBODIMENTS

It will be readily understood that the components of the embodiments as generally described and illustrated in the figures herein can be arranged and designed in a wide variety of different configurations. Thus, the following more detailed description of various embodiments, as represented in the figures, is not intended to limit the scope of the invention, as claimed, but is merely representative of various embodiments. While the various aspects of the embodiments are presented in drawings, the drawings are not necessarily drawn to scale.

The phrases "connected to," "coupled to" and "in communication with" refer to any form of interaction between two or more entities, including mechanical, electrical, magnetic, electromagnetic, fluid, and thermal interaction. Two components may be coupled to each other even though they are not in direct contact with each other. The term "abutting" refers to items that are in direct physical contact with each other, although the items may not necessarily be attached together.

The present invention relates to catheters. In more particular, the present invention relates to a catheter having a radiopaque marker. The radiopaque marker is disposed on the distal end of the catheter in connection with the drainage bores of the catheter. The marker is configured to allow a practitioner to quickly, simply and reliably identify the location of a drainage bore of a drainage catheter. The radiopaque marker is associated with the catheter tube such that utilization of the radiopaque marker band does not increase an outer diameter or decrease an inner diameter of the tube at the location of the radiopaque marker.

Figure 1:
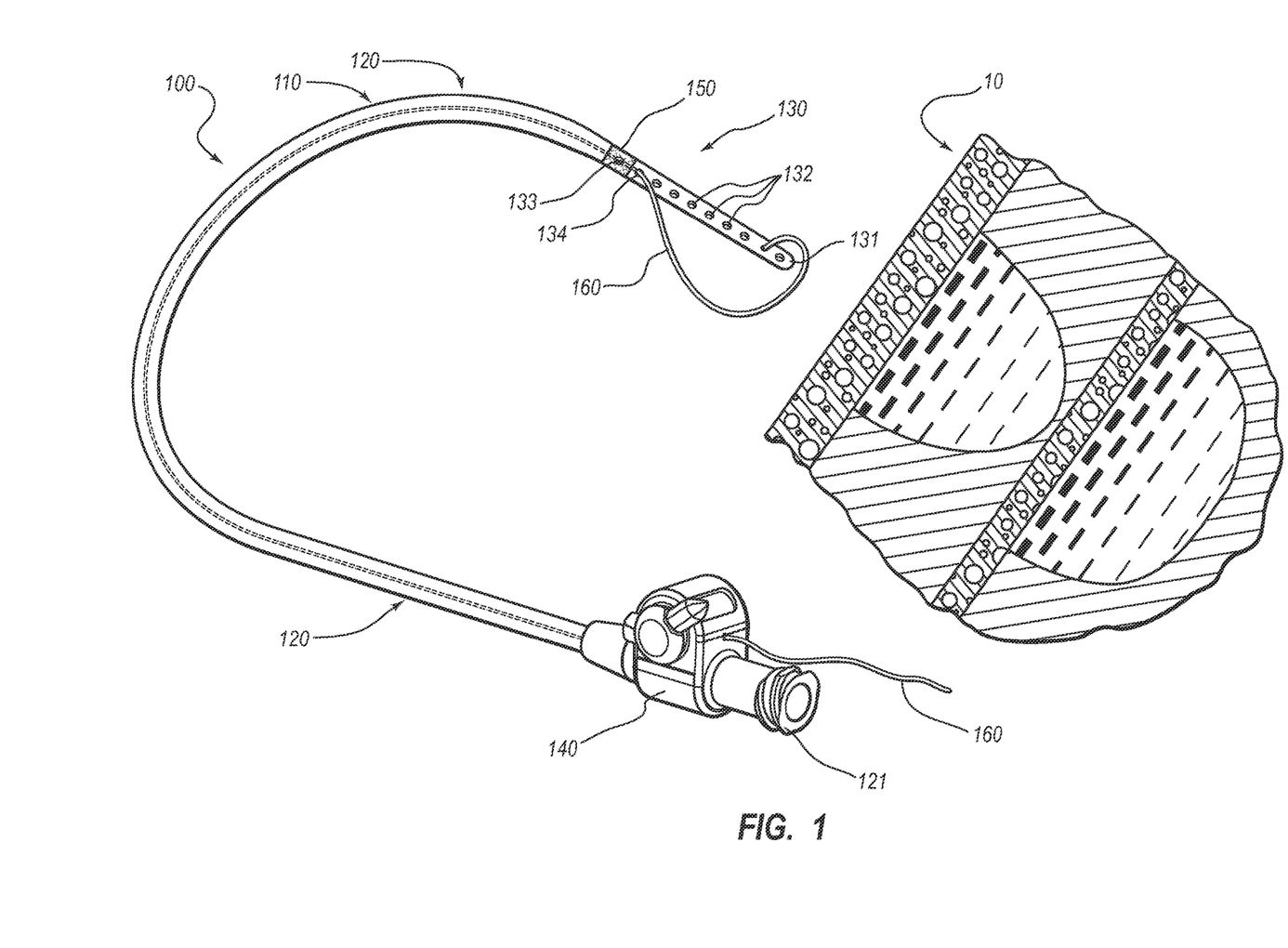
FIG. 1 is a perspective view of a catheter having a radiopaque marker band according to one embodiment of the present invention.

FIG. 1 is a perspective view of one embodiment of a catheter 100 before the catheter has been inserted into a patient 10. Catheter 100 is configured to be utilized for potentially prolonged periods to either deliver fluids to a patient or drain fluid from a patient. Catheter 100 comprises an elongate tube 110 having a proximal end 120 and a distal end 130. Catheter 100 may further comprise a hub 140, a radiopaque marker 150 and a suture 160.

Elongate tube 110 comprises an elongated tubular member having a lumen for allowing the passage of fluid from distal end 130 to proximal end 120. The configuration of elongate tube 110 allows fluid to be drained from a patient 10 to hub 140. Elongate tube 110 comprises a plastic material such as carbothane, polyolefin, polyurethane, or PVC or may be manufactured using any other suitable material for the formation of flexible elongate catheter tubes.

In the illustrated embodiment, proximal end 120 includes an adapter 121 configured to couple a storage vessel, disposal vessel, vacuum system, syringe, infusion pump, or insufflation device to elongate tube 110. In the illustrated embodiment, adapter 121 comprises a luer coupler. Proximal end 120 may also include a hub 140 which is configured to provide a mechanism or member that allows a user to selectively secure a suture 160 to maintain an anchor configuration of a distal end 130 of elongate tube 110. Adapter 121 may be disposed on hub 140 or may comprise a contiguous extension of proximal end 120 of elongate tube 110.

Distal end 130 is configured to be inserted into a body cavity, tissue, or tubular organ system of a patient 10. Distal end 130 may comprise a distal tip 131, a plurality of bores 132, and a radiopaque marker 150. In the embodiment depicted in FIG. 1, distal end 130 is in a straightened configuration to facilitate the introduction of distal end 130 into a body cavity of a patient.

When elongate tube 110 has been inserted into patient 10, radiopaque marker 150 allows a practitioner to readily identify the location of a first bore 133 using an X-ray or another type of radiograph. In the illustrated embodiment, radiopaque marker 150 comprises a band of material that is circumferentially disposed around the diameter of elongate tube 110. Radiopaque marker 150 is aligned on elongate tube such that a first drainage bore 133 is positioned within the middle of radiopaque marker 150. For illustrative purposes, radiopaque marker 150 is depicted as being of a darker color than the surrounding materials; however, the particular coloration of the radiopaque marker be selected from a variety of colors including the color of the other portions of elongate tube 110.

The radiopaque materials selected to form radiopaque marker 150 may comprise a cylindrical polyurethane material imbued with one or more radiopaque materials, such as metal, metal flakes, or metal powder. The particular radiopaque materials typically will be selected based on the type of imaging techniques utilized to identify the location of the radiopaque marker band. During manufacture, the band comprising radiopaque marker 150 is placed over an end of elongate tube 110 and slid to a predetermined position. The polymeric material forming radiopaque marker 150 is then heat fused to the elongate tube 110. Once radiopaque marker band is integrally coupled to elongate tube 110, drainage bores 132 can be formed in distal end 130.

Figure 4:
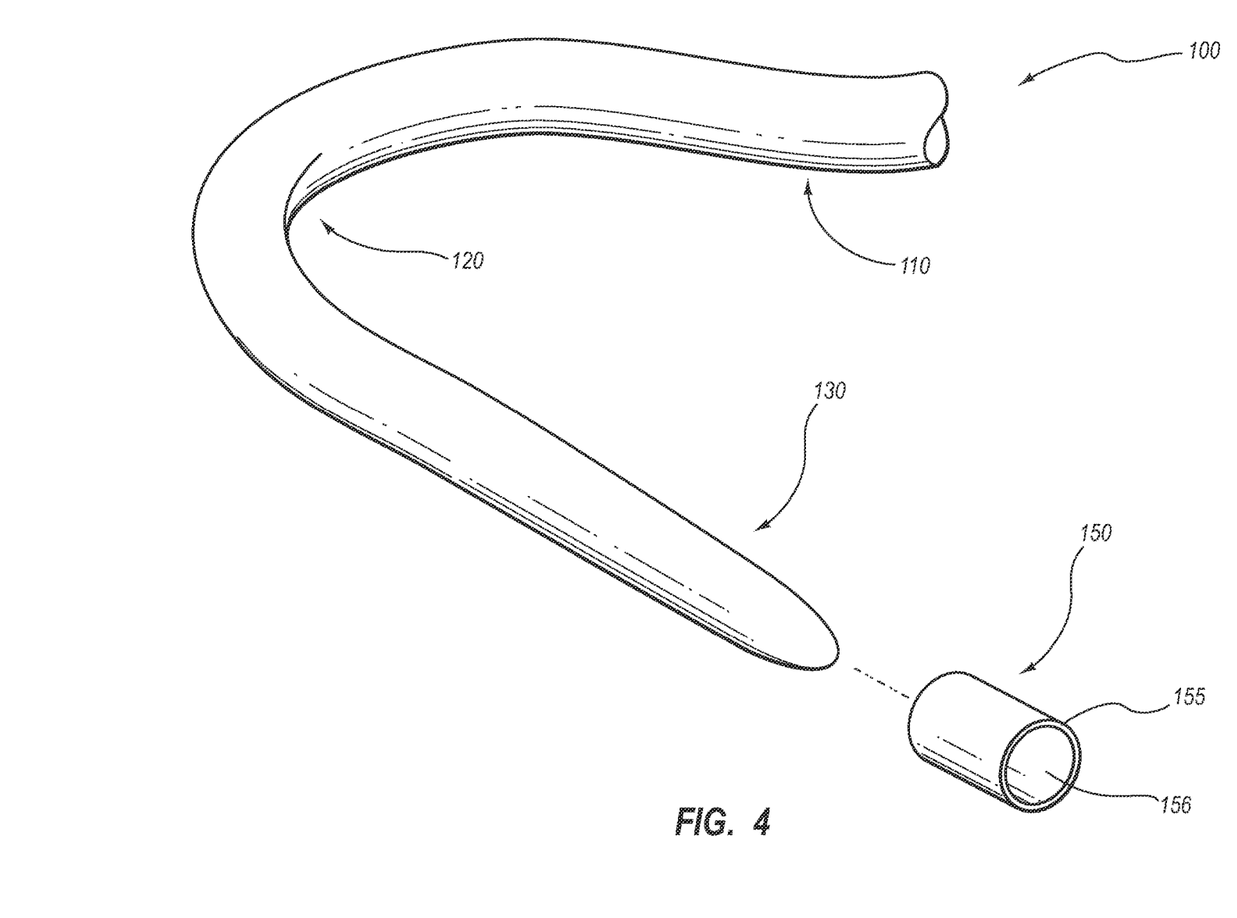
FIG. 4 is a perspective view of a marker band prior to assembly with the catheter tube.

According to one aspect of the present invention, radiopaque marker 150 is manufactured by mixing a predetermined amount of radiopaque material with a solution of dissolved polyurethane. The slurry can be formed into a circumferential band to form the configuration of radiopaque marker 150 utilizing extrusion or other manufacturing processes. One example of a circumferential band configuration of radiopaque marker 150 is depicted in FIG. 4. Radiopaque marker 150 may be subjected to additional manufacturing process to add a superficial layer of material such that no metal or other radiopaque material comes into contact with any of the patient's tissues or fluids. The superficial layer of materials allows radiopaque marker 150 to have a desired thickness while limiting the interposition of a full tube or other layer over the entire marker band which could interfere with the desired level of radiopacity and/or the ability to sufficiently visualize the marker band.

In the illustrated embodiment, suture 160 is utilized in connection with elongate tube 110 and hub 140. Suture 160 is adapted to facilitate and maintain the formation of an anchor loop in distal end 130 of elongate tube 110. Suture 160 runs from hub 140, along the length of elongate tube 110. Suture 160 then exits elongate tube 110 at a suture exit bore 134, which may or may not be the same as first bore 133. In the illustrated embodiment, suture 160 is utilized to allow securement of distal tip 131 of elongate tube 110. In the illustrated embodiment, hub 140 is configured to allow for securement and/or release of suture 160.

As will be appreciated by those skilled in the art, a variety of types and configurations of catheters can be utilized for delivering or draining fluids to or from a patient without departing from the scope and spirit of the present invention.

For example, in one embodiment the drainage catheter is be adapted to be positioned adjacent to an organ, in the vasculature of a patient, or within an organ system, such as the urinary or billiary systems. In another embodiment, the drainage catheter is introduced utilizing a guide wire or rigid stylet. In yet another embodiment, the elongate tube has a constant outer diameter, including the distal end and tip of the elongate tube. The cross sectional shape, length, and diameter of elongate tube 110 and distal end 130 as depicted by the figures herein are provided for exemplary purposes and should not be considered to limiting in nature.

Figure 2:
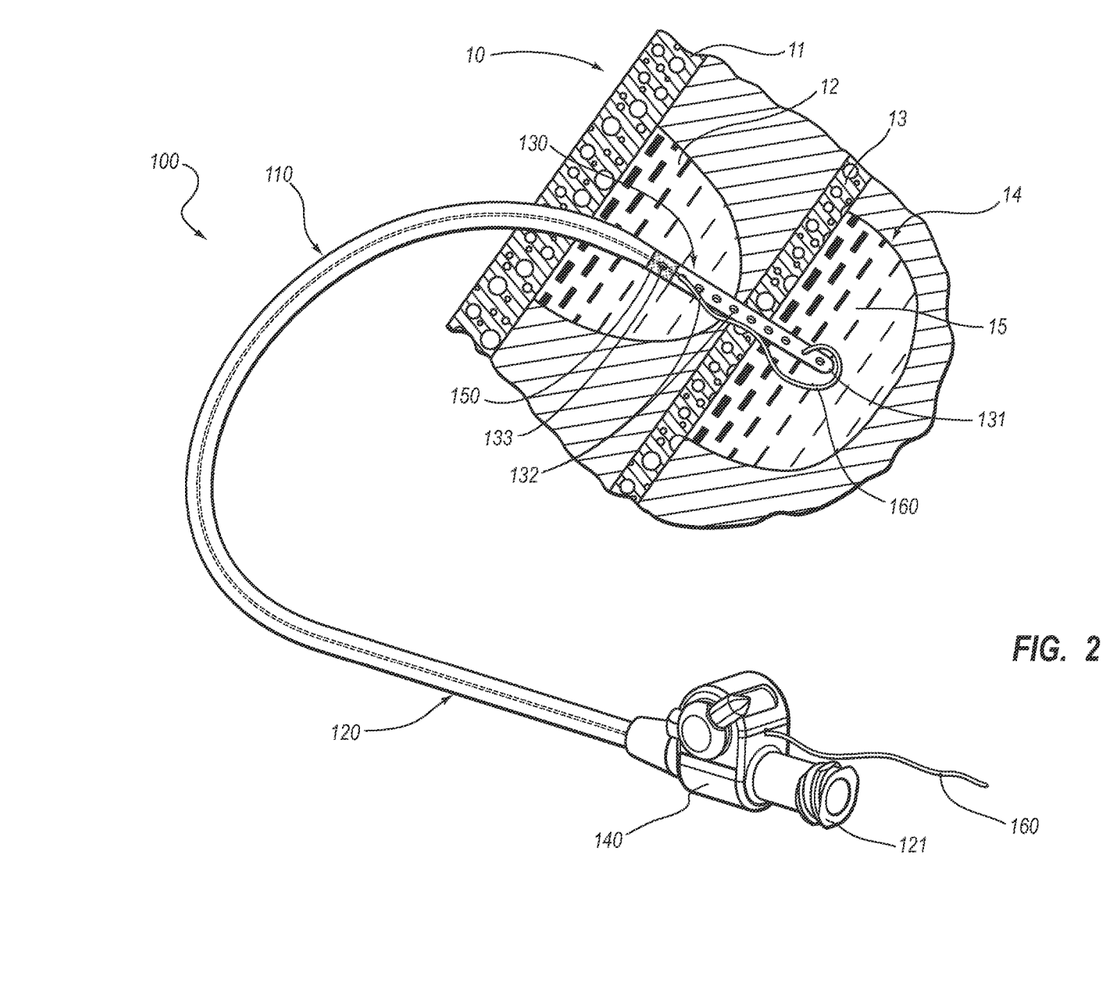
FIG. 2 is a perspective view of the catheter of FIG. 1, wherein the drainage catheter and radiopaque marker band is inserted into a patient.

FIG. 2 is a perspective view of catheter 100 shown in FIG. 1 illustrating insertion of catheter 100 into a patient 10. In the illustrated embodiment, distal tip 131 of end 130 has been inserted through first tissue 11, first cavity 12, second tissue 13, and into second cavity 14. Second cavity 14 contains a volume of fluid 15 which is to be drained from the patient.

As a practitioner inserts catheter 100 into patient 10 to the position depicted in FIG. 2, fluid 15 may begin to drain via the lumen of elongate tube 110. This may lead the practitioner to believe that distal end 130 is properly positioned within patient 10. An unwanted condition may exist, wherein the distal end and in more particular the drainage bores span more than one patient cavity or tissue. Such a condition is depicted in FIG. 2, wherein distal end 130 and drainage bores 132 span both first and second cavities 12 and 14. In this case, fluid 15 may be drained from second cavity 14 into first cavity 12, as well as being drained out of patient 10 via catheter 100.

In the illustrated embodiment, upon employing X-ray or other radiographic or suitable imaging technique, a practitioner can identify the location of radiopaque marker 150 and first bore 133 within patient 10. Further, the practitioner will simply, quickly and reliably determine that the location of the remaining bores 132 based on the fact that radiopaque marker 150 is positioned at the first bore 133. As a result, the practitioner can ascertain that the entire distal end 130 including first bore 133 is not fully positioned within fluid 15 of second cavity 14. Radiopaque marker 150 is configured such that neither an inner diameter nor an outer diameter of elongate tube 110 is altered. In this way, neither the insertion of elongate tube 110 nor the drainage of fluid 15 via the lumen of the catheter tube is encumbered by the presence of radiopaque marker 150.

One example of a complication that can develop based on the situation depicted in FIG. 2 relates to drainage of fluid volumes in the vicinity of a patient's kidney. In the event that the first bore is positioned adjacent the patient's kidney while the other drainage bores are positioned within a volume of fluid to be drained that is not in the tissue surrounding the patient's kidney, fluid can drain from the fluid volume and into the tissue surrounding the patient's kidney. Not only can this interfere with desired drainage of the fluid out of the patient's body, but the transfer of fluid to the tissue surrounding the patient's kidney can create additional complications. For example, the introduction of additional fluid around the patient's kidney can cause undesired pressure on the kidney as a result of the drainage procedure. By being able to identify the precise location of first bore 133 within the patient, proper drainage of bodily fluids can be facilitated. As a result, the practitioner does not have to rely on guess work to determine the location of first bore 133 that could result in undesirable drainage such as to the tissue surrounding the patient's kidney.

Figure 3:
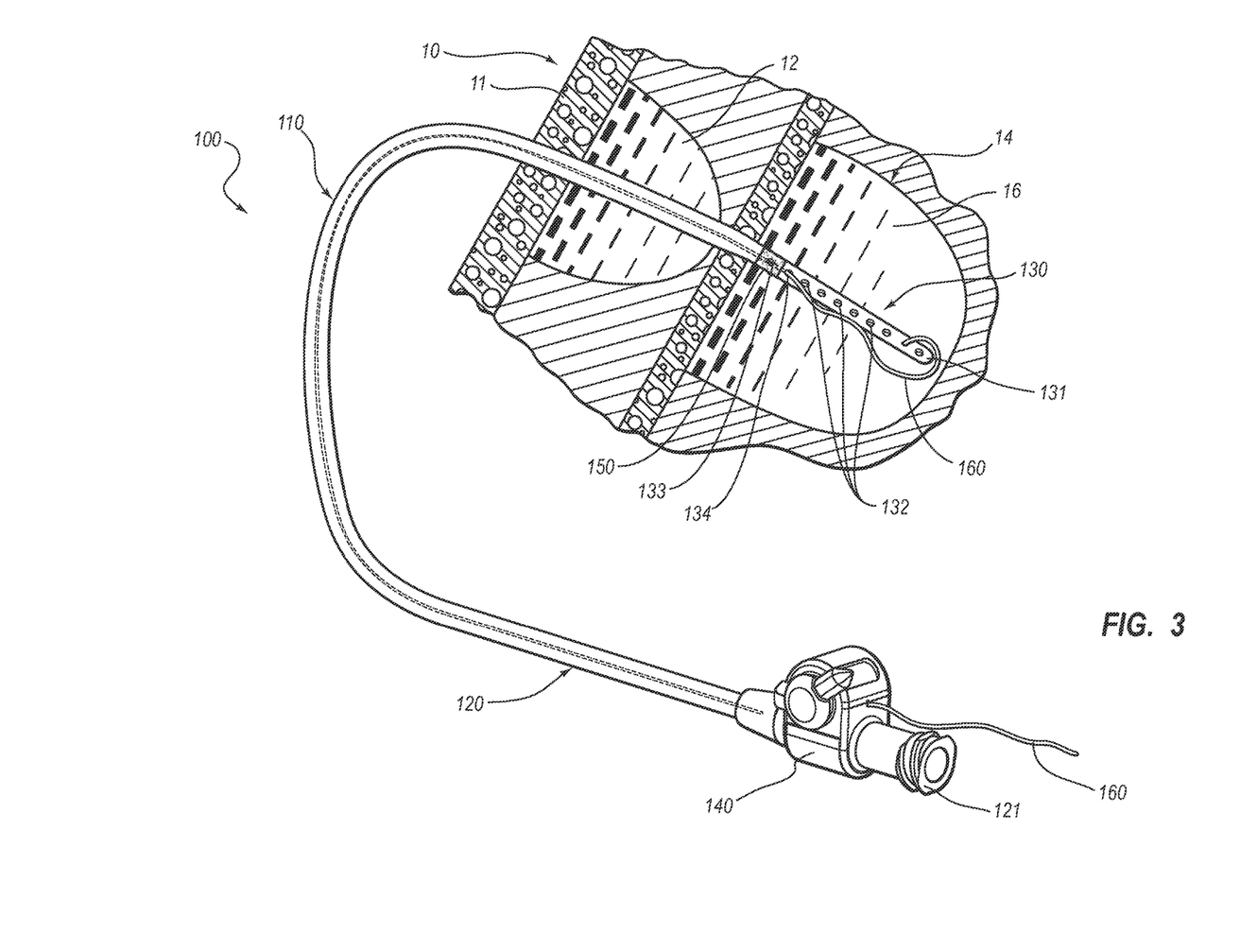
FIG. 3 is a perspective view of the catheter of FIG. 1, wherein the drainage catheter is inserted further into a patient such that the marker band is positioned within a desired fluid volume.

FIG. 3 is a perspective view of drainage catheter 100 shown in FIG. 1, illustrating insertion of distal end 130 into a target cavity 14 of the patient 10. According to one aspect of the present invention, the positioning of drainage catheter 100 depicted in FIG. 3 may represent a stage of an insertion procedure subsequent to the stage depicted in FIG. 2 pursuant to which elongate tube 110 has been advanced further into the patient. Alternatively, the positioning of distal end 130 depicted in FIG. 2 may represent a first attempt of inserting elongate tube 110 into patient 10 while FIG. 3 represents a repositioning of elongate tube 110 into the patient subsequent to an imaging or drainage procedure.

In the illustrated embodiment, distal end 130 of elongate tube 110 has been fully inserted into second cavity 14. Second cavity 14 contains a volume of fluid to be drained 16 from patient 10. The entire distal end of elongate tube 110, from radiopaque marker 150 to distal tip 131, has been advanced into cavity 14. Thus, all of drainage bores 132, including first bore 133, are disposed within the target cavity 14 minimizing the passage of fluid 15 from second cavity 14 into first cavity 12 via elongate tube 110. As described with reference to FIG. 2, the location of distal end 130 within target cavity 14 may be confirmed based on radiopaque imaging of the position of radiopaque marker 150 using radiography or some other appropriate imaging technique.

Once the desired position of distal end 130 and first bore 133 has been achieved, the practitioner can then secure the position of distal end 130 within the patient. To maintain the desired positioning of distal end 130 within body cavity 14 of patient 10, the practitioner forms an anchor loop structure in the distal end by grasping and pulling the portion of suture 160 extending proximally from hub 140 in a rearward direction. This draws distal tip 131 of elongate tube 110 to a suture bore 134. The suture bore 134 to which distal tip 131 is drawn may or may not be the same bore as first bore 133. Suture bore 134 is positioned at a point on elongate tube 110 where suture 160 exits the side wall of elongate tube 110 and proximally to distal tip 131. As suture 160 draws tip 131 to suture exit bore 134, distal end 130 forms a pigtail type anchor loop configuration. The anchor loop configuration in distal end 130 of elongate tube 110 maintains the position of distal end 130 within body cavity 14 even where the wall of the body cavity is insufficiently rigid to secure other catheter securement devices.

Hub 140 may be configured to securely maintain tension on suture thread 160, thereby maintaining distal end 130 in an anchor loop configuration. Additionally, hub 140 may be configured to allow for release of tension on the suture thread, thereby allowing a practitioner to release distal end 130 from the anchor loop configuration. Once distal tip 131 of elongate tube 110 is positioned and anchored within the patient, the catheter may remain within the body of the patient for a desired period of time to facilitate ongoing drainage or delivery of fluids.

Drainage bores 132 may be positioned on distal end 130 such that when distal end 130 is in the anchor loop configuration, the drainage bores are disposed on the inside diameter of the loop. When drainage bores 132 are positioned on the inside diameter of distal end 130, contact by the walls of body cavity 14 on distal end 130 does not obstruct drainage of the volume of fluid 15 from body cavity 14. This can be particularly helpful where the drainage of bodily fluid 15 causes collapse of the walls of body cavity 14 during operation of drainage catheter 100.

As will be appreciated by those skilled in the art, a variety of types and configurations of catheter hubs for generating, maintaining and releasing tension on a suture thread may be utilized without departing from the scope and spirit of the present invention. Further, any catheter hub, catheter member, or technique for generating, maintaining, and releasing tension on a suture thread can be used with the present invention.

Further, one skilled in the art will appreciate that a variety of devices or techniques may be used for maintaining the position of a catheter once the catheter is inserted into a patient that do not comprise a pigtail anchor loop. For example, in one embodiment, the distal end of the catheter may be surgically attached to a wall of a body cavity within a patient. Alternatively, all or a portion of the catheter that is not inside a patient may be immobilized using suture, adhesive patch, catheter securement mechanism, or any other suitable technique.

FIG. 4 is a perspective view of components of drainage catheter 100 shown prior to assembly and fusion of radiopaque marker 150 to elongate tube 110. In the illustrated embodiment, radiopaque marker 150 comprises a marker band. Radiopaque marker 150 comprises side wall portions 155 and a lumen 156. Wall portions 155 are disposed opposite each other and have a circular transverse cross section. The height of wall portions 155 defines a thickness of the material that comprises radiopaque marker 150. Radiopaque marker 150 is configured such that lumen 156 has an inner diameter that is greater than an outer diameter of distal end 130 of elongate tube 110.

During assembly of catheter 100, radiopaque marker 150 is slid over tip 131 such that tip 131 is received by lumen 156 of the marker band. Radiopaque marker 150 can then be advanced proximally up elongate tube 110 to a predetermined position where it can be heat fused to elongate tube 110. In the illustrated embodiment, radiopaque marker 150 is formed from a material that can be heat fused to elongate tube 110 providing for integral coupling of radiopaque marker 150 to elongate tube 110. By utilizing a radiopaque marker 150 in a band configuration, assembly of radiopaque marker 150 relative to elongate tube 110 can be effectuated in a simple and cost effective manner.

As will be appreciated by those skilled in the art, a variety of types and configurations of radiopaque markers can be utilized without departing from the scope and spirit of the present invention. For example, according to one embodiment of the present invention, the radiopaque marker comprises a marker strip which is wrapped around the elongate tube and then heat welded to the elongate tube. In another embodiment, the marker band comprises strips of radiopaque material, which may be roughly rectangular in shape, wherein the longitudinal axis of the radiopaque material strips are aligned with the longitudinal axis of the catheter tube. In another embodiment, the strips of radiopaque material are interposed on either side of the first drainage bore. In alternative embodiments, the marker band may not comprise a full cylinder, but rather may comprise more or less than half of a cylinder. In yet another embodiment, the radiopaque material may be contained within a void that is formed within the marker band.

Additionally, as will be appreciated by those skilled in the art, alternative manufacturing processes may be employed to produce either a catheter with a marker band, or a marker band alone. For example, in one embodiment, a radiopaque material/plastic slurry may be co-extruded with an additional superficial layer of material. In a different embodiment, the radiopaque material/plastic slurry may be co-extruded with the main catheter tube, such that the marker band forms an integral portion of the catheter tube.

In addition to the different possible conformations and configurations of radiopaque marker bands, one skilled in the art will appreciate that a variety of materials may comprise a radiopaque marker without departing from the scope and spirit of the present invention. For example, in alternative embodiments the radiopaque material may comprise one or more types of metal flakes, powder, or a combination of flakes and powder, such as gold, silver, platinum, lead, or tungsten. In another embodiment, the radiopaque material may comprise ceramics or ceramics powder mixed with a plastic material to form a marker band. In yet another embodiment, the radiopaque material may comprise Barium Sulfate, Bismuth Subcarbonate, Bismuth oxychloride or Bismuth trioxide. The selected amounts of radiopaque material which may be suitable for marking a catheter will typically vary depending on a number of different factors, including how deeply within a patient the catheter tube will be located, the density of the tissues surrounding the catheter tube, the size of the catheter tube, etc. Likewise, concentrations or ratios of radiopaque material which are imbedded within the plastic material may vary within a wide range of values due to the above cited considerations, as well as constraints regarding manufacturing processes and desired physical properties of the marker band. Thus, by way of example and not by way of limitation, the weight to weight percentage ratio of Barium Sulfate, Bismuth Trioxide, or Bismuth Subcarbonate to polyurethane may vary from about 20/80 to about 50/50. In some applications, the weight to weight percentage ratio may be up to about 75%.

Additionally, one skilled in the art will recognize that using different radiopaque materials within a single marker band may allow for areas of differential X-ray shielding. Likewise, using different amounts or concentrations of a single radiopaque material in different areas of a marker may give rise to areas of disparate radiopacity. By varying the types, amounts, or concentrations of radiopaque material information, such as directionality, may be conferred upon the marker, and subsequently communicated to a practitioner viewing a radiograph.

Figure 5:
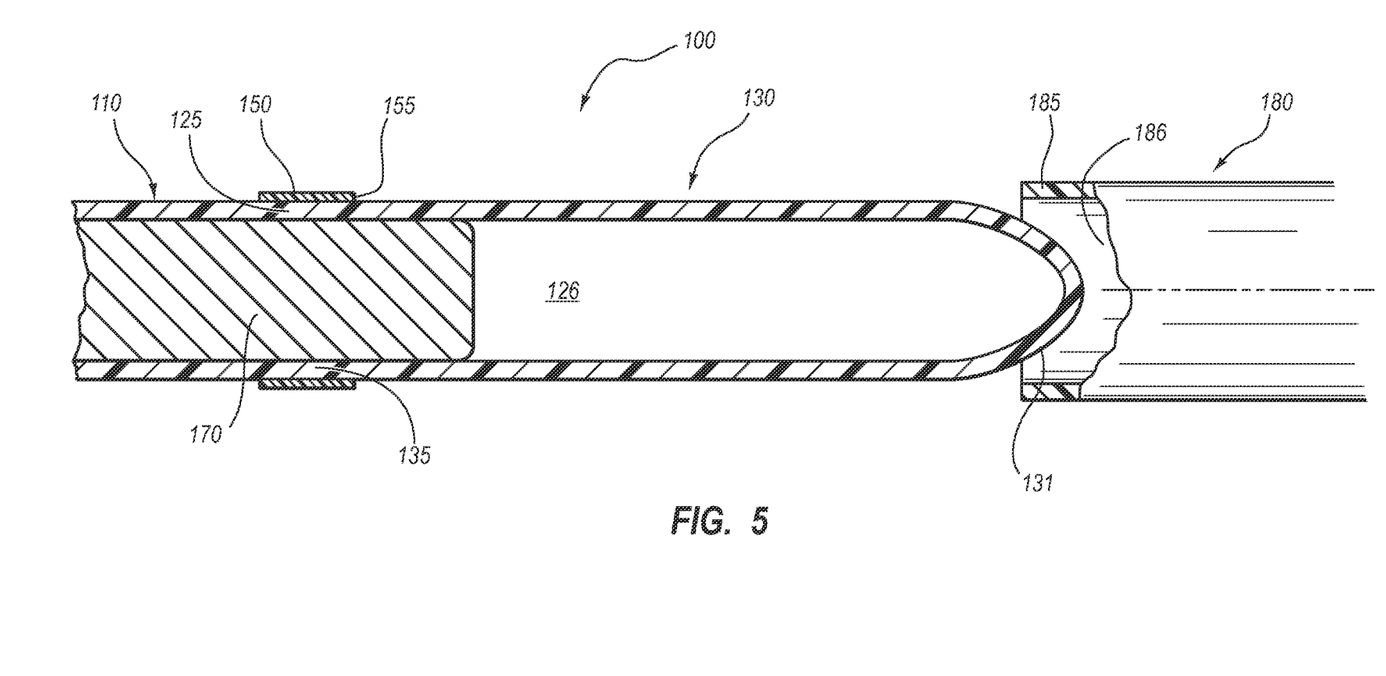
FIG. 5 is a longitudinal cross-section view of the catheter shown in FIG. 4 illustrating a mechanism for integrating the marker band into the catheter tube.

FIG. 5 is a longitudinal cross-section view of the components of catheter 100 after radiopaque marker 150 has been positioned over elongate tube 110 and before heat fusion of radiopaque marker 150 to elongate tube 110. In the illustrated embodiment, radiopaque marker 150 is disposed adjacent to and circumferentially around wall portions 125 and 135 of distal end 130 of elongate tube 110. In the depicted embodiment, radiopaque marker 150 has been advanced over distal tip 131 and in the direction of proximal end 120 (see FIG. 2) to a predetermined position.

Radiopaque marker 150 can be configured to form an interference or friction fit with elongate tube 110 such that radiopaque marker 150 can be retained on the tube during assembly. For example, the band forming radiopaque marker 150 may have a slightly smaller diameter than the outer diameter of elongate tube 110. In this embodiment, during assembly radiopaque marker 150 is stretched, heated or otherwise forced over elongate tube 110 until it is in a desired position. Once radiopaque marker 150 is in the desired position relative to elongate tube 110, the radiopaque marker 150 is unstretched, cooled or otherwised allowed to remain in a fixed position relative to elongate tube.

The width of radiopaque marker 150 can be selected from any suitable width and may be selected according to different parameters of the catheter tube. For example, in one embodiment the band has a width of approximately 5 cm. Likewise, the height of radiopaque marker 150 as depicted by wall 155 in FIG. 5 is strictly for illustrative purposes and may vary according to different embodiments.

Prior to the heat fusion of radiopaque marker 150 to elongate tube 110, a mandrel or plug 170 may be inserted into lumen 126 of elongate tube 110. Mandrel 170 is configured to maintain the inner diameter of elongate tube 110 and lumen 126 during and after heat fusion. After heat fusion, mandrel 170 may be removed via a proximal end of elongate tube 110.

A confinement tube 180 may be used to maintain the outer diameter of elongate tube 110 during and after heat fusion. In the illustrated embodiment, confinement tube 180 is comprised of a piece of metal with one or more open ends, wall portions 185 and a lumen 186. Confinement tube 180 is configured to receive at least those portions of elongate tube 110 that are adjacent to radiopaque marker 150. According to one embodiment of the present invention, confinement tube 180 comprises a precision bore glass tube which is sized to approximate the elongate tube 110. The confinement tube 180 allows the unrestricted passage of the elongate tube 110 to the point where the unfused radiopaque marker 150 has been placed.

Confinement tube 180 is utilized to maintain the outside diameter of elongate tube 110. In one embodiment, confinement tube 180 is forced over radiopaque marker 150 mechanically compressing the marker 150 to elongate tube 110. Heat is applied until the materials soften and the outside diameter of elongate tube 110 approximates the inside diameter of confinement tube 180. In one illustrative embodiment, additional lateral force is applied to elongate tube 110 on either side of the confinement tube 180 placing additional compressive force on elongate tube 110 and marker 150 fusing the components into a single component. The assembly is cooled and removed from the confinement tube 180 and the mandrel 170 is removed from within the elongate tube 110.

One or both of mandrel 170 and confinement tube 180 can comprise heat sources for applying heat to fuse or weld radiopaque marker 150 to elongate tube 110. Alternatively, heat may be applied to the confinement tube or directly to elongate tube 110, radiopaque marker 150, or both elongate tube 110 and radiopaque marker 150 by an external source. During the heat fusion process, radiopaque marker 150 and/or portions of elongate tube 110 that are touching radiopaque marker 150 may become softened, or partially liquefied, such that the marker band can be embedded, fused to and/or fixedly attached to elongate tube 110. During the heat fusion process, radiopaque marker 150, and elongate tube 110 are configured such that the marker 150 and tube 110 fuse together, and wall 155 of radiopaque marker 150 becomes contiguous with wall portions 125 and 135 of the elongate tube 110.

A number of advantages are provided by the integral coupling of the band forming radiopaque marker 150 into elongate tube 110. For example, the radiopaque marker can be integrated into the length of elongate tube 110 without requiring the interposition of multiple tube sections to sandwich or otherwise protect elongate radiopaque marker 150. Not only does this allow for the visualization of radiopaque marker 150 more clearly relative to the outside diameter of elongate tube 110, but the cost and complexity of manufacturing the marker band is greatly reduced. As a result, the radiopaque marker 150 can be manufactured more efficiently and cost effectively while providing an improved catheter product to the practitioner.

Because radiopaque marker 150 can be heat welded into the length of elongate tube 110, radiopaque marker 150 does not decrease the inside diameter or increase the outside diameter of elongate tube 110. Additionally, the formation of ridges or profiles on the inside or outside diameter of elongate tube 110 is avoided. As a result, introduction of the of the elongate tube 110 into the patient can be conducted simply and efficiently without catching of an exposed ridge of a marker band. Similarly, fluid can drain through elongate tube without forming a ridge or narrowing the inside diameter of elongate tube which could catch tissue contained within the drainage fluid or which could cause obstruction or slowing of the drainage of fluid from the patient. By utilizing a marker band which is heat welded into the length of elongate tube 110, costly techniques or manufacturing processes which could affect the durability or compromise the strength or integrity of the elongate tube 110 are also avoided.

As will be appreciated by those skilled in the art, a variety of types and configurations of heat fusion processes and heat sources can be utilized for fusion of a plastic marker band that is loaded with radiopaque material to a plastic catheter tube without departing from the scope and spirit of the present invention. For example, the temperature, heating time, cooling and other parameters of the assembly can be tailored based on the materials utilized, the mass of the assembly and other variables related to the catheter and/or the marker. In alternative embodiments, the heat fusion process may accomplished by using RF welding, forced hot air, a quartz heating lamp, or any other suitable concentrated, localized heat source.

One skilled in the art will also appreciate that a variety of types and configurations of confinement tubes can be utilized during a heat fusion process such that after the heat fusion process the marker band comprises the same outer diameter as the outer diameter of the catheter tube, and adjacent portions of the catheter tube do not increase their outer diameter. For example, in one embodiment a clamshell type confinement tube is used, such that in a closed configuration the clam-shell confinement tube comprises an inner diameter that is the same as the outer diameter of the area of the catheter tube to which the marker band is to be fused. Before heat fusion, the catheter tube with the marker band, which is disposed at a predetermined position on the catheter tube, are placed in the clam-shell confinement tube. The clamshell may not fully close because the marker band adds to the outer diameter of the catheter tube. As the marker band becomes fused to the catheter tube during the heat fusion process, the clamshell confinement tube may be able to fully close. The clamshell confinement tube of this embodiment may comprise a heat source and may be used in conjunction with a mandrel.

Figure 6A:
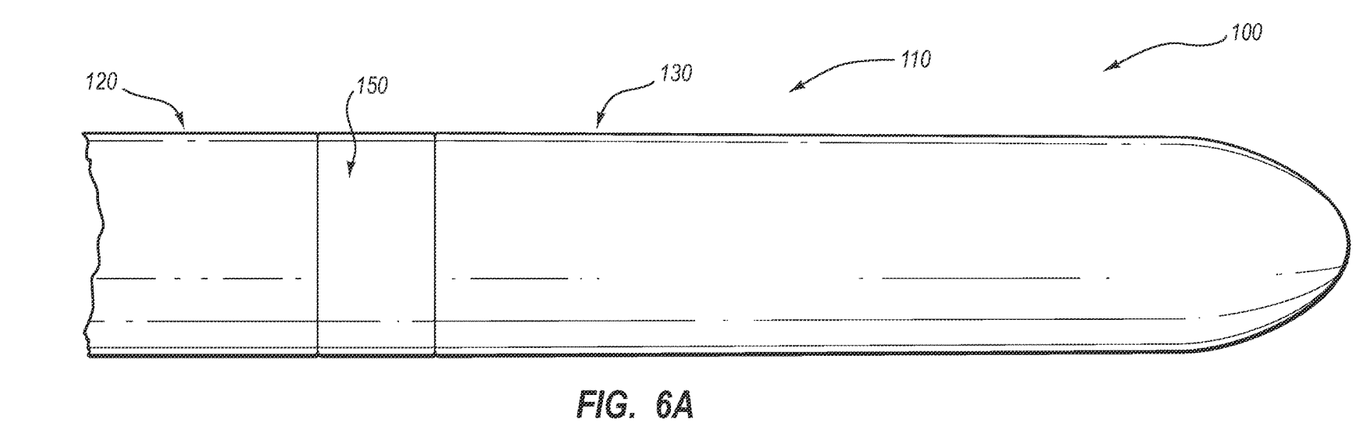
FIG. 6A is a side elevation view of the catheter of FIG. 5 after the radiopaque marker band has been heat fused to the catheter tube.

FIG. 6A is a side elevation view of the portions of catheter 100 shown in FIG. 5 after heat fusion. Once radiopaque radiopaque marker 150 has been joined by heat fusion to elongate tube 110, radiopaque marker 150 is integrally coupled to elongate tube. In other words, catheter 100 comprises a single elongate tube 110 that includes a radiopaque marker 150. During the heat fusion process, radiopaque marker 150 and elongate tube 110 have become contiguous. Since the fusion process is configured to maintain the outer diameters of portions 120 and 130, elongate tube 110 can have a consistent outer diameter along its entire length. Thus, the boundaries of radiopaque marker 150 depicted in FIG. 6A may no longer be identified by a ridge, line, or other distinguishing characteristic.

Figure 6B:
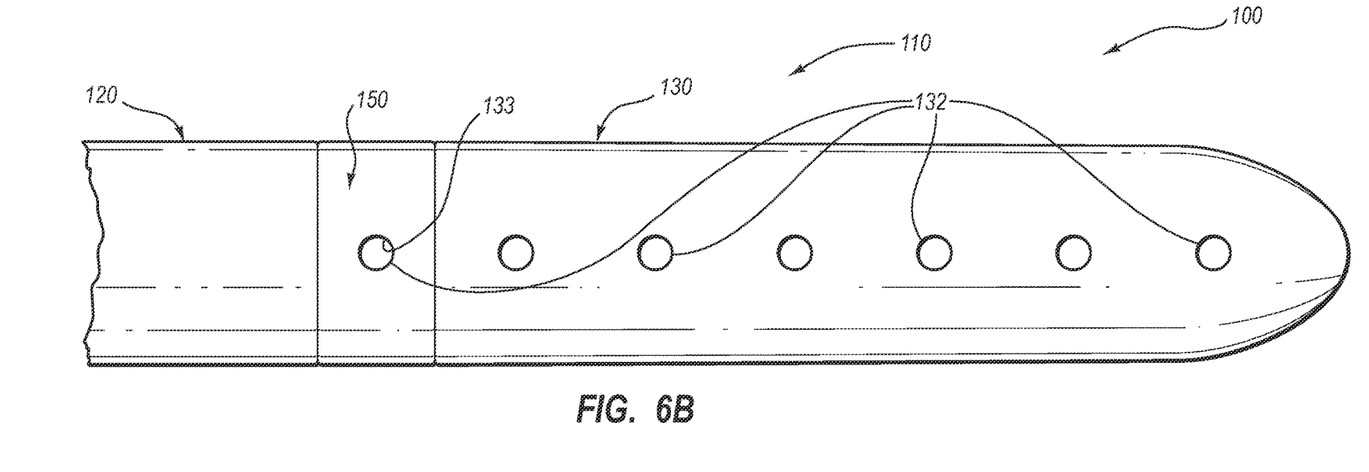
FIG. 6B is a side elevation view of the catheter of FIG. 6A after bores have been formed in the catheter tube and marker band.

FIG. 6B is a side elevation view of the portions of catheter 100 shown in FIG. 6A after drainage bores 132 have been formed in elongate tube 110. According to one aspect of the present invention, after heat fusion of radiopaque marker 150 to elongate tube 110, drainage bores 132 may be punched in distal end portion 130 such that the bores are in fluid communication with lumen 126 depicted in FIG. 5. Lumen 126 (FIG. 5), is in fluid communication with the aperture exiting from adapter 121 disposed on proximal end 120 of elongate tube 110 (see FIG. 1). As a result, when catheter 100 is inserted into a patient, bores 132 are in fluid communication to the outside of the patient.

According to one aspect of the present invention the material properties of marker 150 are similar to the material properties of elongate tube 110. In other words, marker 150 and elongate tube 110 are made from elastomers which exhibit similar properties of flexibility, resilience and response to tooling, heat and other manufacturing processes. As a result, a drainage bore can easily, simply and efficiently be formed through both marker 150 and elongate tube 110 utilizing punching, drilling or heat puncturing without causing deformation, tearing or other unwanted structural changes to the catheter 100. As a result, a single drainage bore 132 is formed through both marker 150 and elongate tube 110 simultaneously or during a single drainage bore 132 creation step. For example, in one illustrative embodiment marker 150 is fused to elongate tube 110 in a first step. In subsequent step, a drainage bore is created through both marker 150 and elongate tube utilizing a punch, drill or heat puncturing mechanism.

By being formed through marker 150 and elongate tube 110, a drainage bores 132 is positioned such that it is circumferentially surrounded by marker 150. In this manner, marker 150 is coextensive with a predetermined drainage bore allowing a practitioner to precisely determine the location of the drainage bore. In one embodiment, the drainage bore 132 associated with marker 150 is the proximal-most drainage bore 132. In this manner, not only can the precise location of the proximal-most drainage bore be identified through imaging techniques, but the relational position of the distally positioned drainage bores 132 can also be determined.

Once a drainage bore 132 has been formed through marker 150 and elongate tube 110, the drainage bore 132 has an outward facing extent which is contiguous with the surface of marker 150 which is positioned on the outside diameter of catheter 100. A lumen of the drainage bore extends through the body of marker 150 and into the body of elongate tube 110. An inward facing extent of drainage bore 132 is contiguous with elongate tube 110 such that the inward facing extent of marker 150 is positioned on the inside diameter of elongate tube 110. In other words, during a single drainage bore formation step, a drainage bore creation tool enters the outward facing surface of marker 150, extends through the body of marker 150, enters the body of elongate tube 110 and exits the inside diameter of elongate tube forming a single and unitary drainage bore through both marker and elongate tube 110.

The outward facing extent of drainage bore 132 will typically be placed in contact with the body cavity of the patient. In the event that catheter 100 is being utilized to drain bodily fluids from the patient, the fluids will first enter into the outward facing extent of drainage bore 132. The fluids will flow from the outward facing extent of drainage bore 132 and flow into the lumen of drainage bore. From the lumen of drainage bore 132, the fluids will pass through the inward facing extent of marker 150 and into the lumen of elongate tube 110. Once the fluids have passed into the lumen of elongate tube 110, they can be drained from the patient.

As will be appreciated by one skilled in the art, the length of the lumen of bores 132 is dictated by the thickness of the wall of the catheter 100. In the illustrated embodiment, the length of the lumen of bores 132 is much shorter than the overall circumference of the drainage bore. The shape of bores 132 can vary from that depicted in FIG. 6B. Further, the bores can be formed by alternative mechanisms to punching, including drilling, or heat puncturing. Alternatively, bores 132 can be formed during manufacturing of distal end 130 such that bores 132 are disposed within elongate tube 110 before marker 150 is fused to the catheter tube.

First drainage bore 133 is formed within radiopaque radiopaque marker 150 such that the bore is approximately centered within the marker band. In the illustrated embodiment, upon employing X-ray or other radiographic or suitable imaging technique, a practitioner can identify the location of radiopaque marker 150 and first bore 133 within patient 10. Further, the practitioner will simply, quickly and reliably determine the location of the remaining bores 132 based on the fact that radiopaque marker 150 is positioned at first bore 133. As a result, the practitioner can ascertain that the entire distal end 130 including first bore 133 is not fully positioned within fluid 15 of second cavity 14. Radiopaque marker 150 is configured such that neither an inner diameter nor an outer diameter of elongate tube 110 is altered. In this way, neither the insertion of elongate tube 110 nor the drainage of fluid 15 via the lumen of the catheter tube is encumbered by radiopaque marker 150.

A number of advantages are provided by the integral coupling of the band forming radiopaque marker 150 into elongate tube 110. For example, the radiopaque marker can be integrated into the length of elongate tube 110 without requiring the interposition of multiple tube sections to sandwich or otherwise protect radiopaque marker 150. Not only does this allow for the visualization of marker band more clearly on the outside diameter of elongate tube 110, but the cost and complexity of manufacturing the marker band is greatly reduced. As a result, the radiopaque marker 150 can be manufactured more efficiently and cost effectively while providing an improved catheter product to the practitioner. Additionally, because radiopaque marker 150 can be heat welded into the length of elongate tube 110, radiopaque marker 150 does not decrease the inside diameter or increase the outside diameter of elongate tube 110. Additionally, the formation of ridges on the inside or outside diameter of elongate tube 110 is avoided. As a result, introduction of the of the elongate tube 110 into the patient can be conducted simply and efficiently without catching of an exposed ridge of a marker band. Similarly, fluid can drain through elongate tube without a forming a ridge or narrowing the inside diameter of elongate tube which could catch tissue contained within the drainage fluid and which could cause obstruction or slowing of the drainage of fluid from the patient. By utilizing a marker band which is heat welded into the length of elongate tube 110, costly techniques or manufacturing processes which could affect the durability or compromise the strength or integrity of the elongate tube 110 are also avoided.

In the illustrated embodiment, a small ridge or groove appears at the edges of marker band 150. It will be appreciated that this small ridge is utilized to show the transition from the edge of the marker band to the tube for the sake of clarity and a similar ridge or groove may or may not be present in the assembled device. For example, a smooth transition that does not include any ridge or groove will typically be provided at the edges of the marker band.

Figure 7:
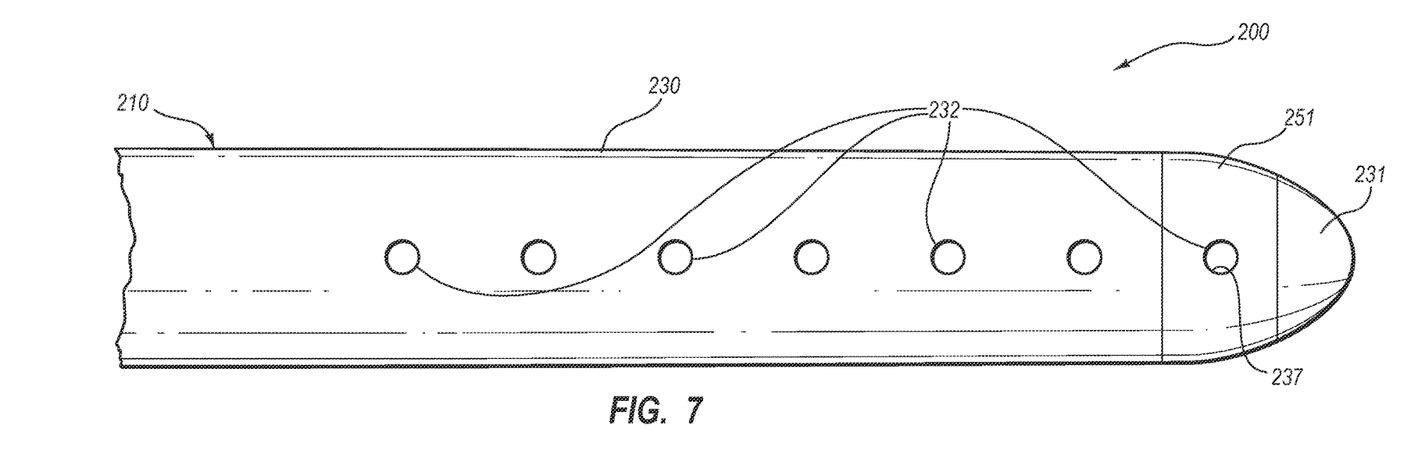
FIG. 7 is a side elevation view of a catheter according to an alternative embodiment of the present invention.

FIG. 7 is a side elevation view of a catheter 200 according to an alternative embodiment of the present invention.

Catheter 200 may be configured similarly and may function similarly to catheter 100, which is described with reference to FIGS. 1-6B. In the illustrated embodiment, catheter 200 comprises a tube 210 that has a distal end 230 and a distal tip 231. A plurality of drainage bores 232 allow for fluid communication between an area adjacent to distal end 230 and a proximal portion of catheter 200.

Radiopaque marker 251 is disposed adjacent to distal tip 231 such that marker 251 is located at a last bore 237. Last bore 237 defines a bore that is more distal than the other bores 232 disposed within distal end 230. Once distal end 230 is located within a body of a patient, the locations of last bore 237 and distal tip 231 may be readily appreciated via radiography due to the properties of marker 251. Radiopaque marker 251 may be configured similarly and may function similarly to radiopaque radiopaque marker 150, which is described herein.

As will be appreciated by those skilled in the art, a variety of types and configurations of radiopaque marker bands and catheter tubes can be utilized without departing from the scope and spirit of the present invention. For example, in one embodiment the marker band extends all the way to the distal tip such that marker band encompasses the entire distal tip of the catheter. In another embodiment, the catheter comprises one bore, which may be disposed adjacent to the distal tip, or at the distal tip. In yet another embodiment, the catheter is configured to infuse a medicament into a patient's vascular or other tubular system via a bore in the catheter tube. In this embodiment, the location of the distal tip may be appreciated based on the presence of the marker band using fluoroscopy. In a related embodiment, the catheter may be configured to allow for insufflation of a medicament into a patient's body.

Figure 8:
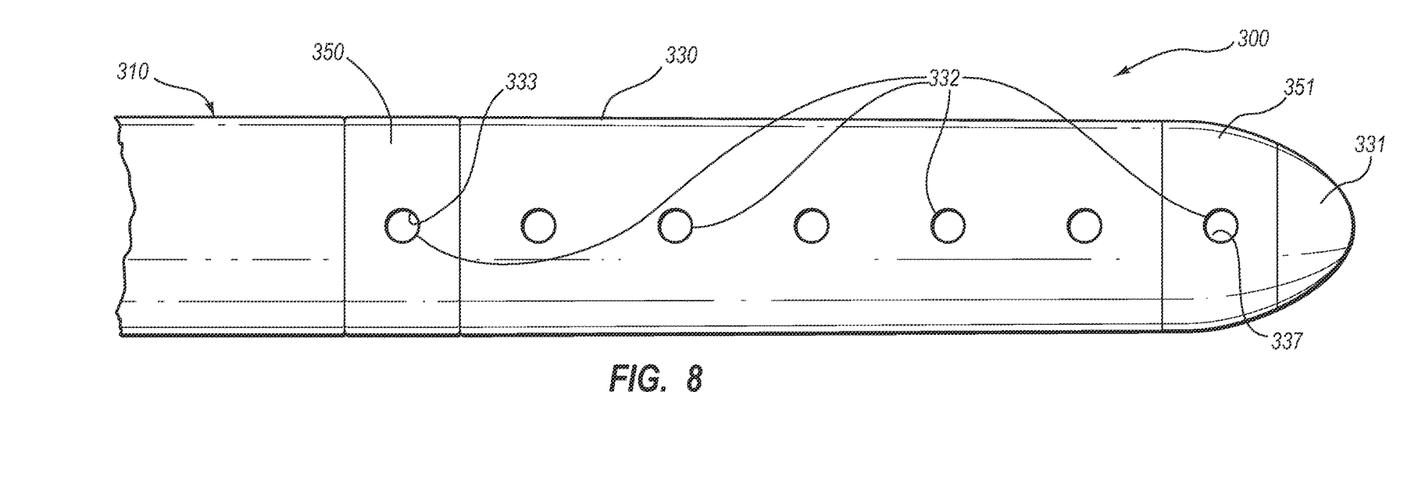
FIG. 8 is a side elevation view of a catheter having a plurality of marker bands according to yet another embodiment of the present invention.

FIG. 8 is a side elevation view of a catheter 300 according to one embodiment of the present invention. Catheter 300 comprises a tube 310 that has a distal end 330 and a distal tip 331. Drainage bores 332 allow for fluid communication between an area adjacent to distal end 330 and a proximal portion of catheter 300.

Catheter 300 comprises two radiopaque markers 350 and 351 which may be configured similarly and may function similarly to radiopaque marker 150, which is described with reference to FIGS. 1-7. Marker band 350 is disposed at a proximal portion of distal end 330. A first bore 333 is positioned through marker band 350. First bore 333 defines a bore that is located more proximal to the remaining bores 332 disposed within distal end 330. Marker band 351 is disposed adjacent to distal tip 331 and may comprise a last bore 337. Last bore 337 defines a bore that is located distally to the remaining bores 332 disposed within distal end 330.

Once distal portion 330 is located within the body of a patient, the location of first bore 332 and last bore 337 may be readily appreciated via radiography due to the properties of markers 350 and 351. The ability to precisely identify the location of one or more bores or other markers of a catheter tube may be particularly useful when a catheter is inserted within or adjacent to a tissue or organ that may be damaged by inappropriate positioning of the catheter. Further, in the case where a catheter is left in a patient for an extended period of time, the marker bands allow for determining whether a distal end of a catheter tube has changed position. As such, the catheters described herein may be useful for researching techniques, hardware, catheter tubes, and catheter tube configurations for anchoring a catheter within a patient such that the position of the catheter tube does not change over time.

The examples and embodiments disclosed herein are to be construed as merely illustrative and not a limitation of the scope of the present invention in any way. It will be apparent to those having skill in the art that changes may be made to the details of the above-described embodiments without departing from the underlying principles of the invention. In other words, various modifications and improvements of the embodiments specifically disclosed in the description above are within the scope of the appended claims. The scope of the invention is therefore defined by the following claims.

The invention claimed is:

1. A catheter adapted to be advanced to a desired position within a patient and having a radiopaque marker to facilitate identification of the placement of the catheter within the patient, the catheter comprising: an elongate tube consisting of a single layer, the elongate tube having a proximal end, a distal end and lumen extending a length thereof, the distal end of the elongate tube adapted to be advanced to a desired position within a patient; at least one drainage bore positioned within the distal end of the elongate tube, the at least one drainage bore adapted to allow passage of fluid to or from the lumen of the elongate tube and the desired position within the patient; and a first radiopaque marker disposed around and integrally coupled to an outside surface of the elongate tube, wherein the first radiopaque marker is configured to be heat fused to the elongate tube using a confinement tube disposed on the outside of the elongate tube and a mandrel disposed within the lumen of the elongate tube, the first radiopaque marker surrounding a portion of the elongate tube such that the first radiopaque marker is configured to come into contact with a body cavity of the patient, and the at least one drainage bore passes through at least a portion of the elongate tube surrounded by the first radiopaque marker surrounding a portion of the elongate tube such that the first radiopaque marker is configured to come into contact with a body cavity of the patient, and the at least one drainage bore passes through at least a portion of the elongate tube surrounded by the first radiopaque marker to allow a practitioner to readily determine a position of the at least one drainage bore utilizing radiopaque imaging, the first radiopaque marker comprised of particles of radiopaque material distributed throughout an elastomeric material and the first radiopaque marker disposed such that an outside diameter of the first radiopaque marker is substantially the same as an outside diameter of the elongate tube adjacent the first radiopaque marker and an inside diameter of the elongate tube at the first radiopaque marker is substantially the same as an inside diameter adjacent to the first radiopaque marker.

2. The catheter of claim 1, wherein the catheter further comprises:
a hub disposed on a practitioner-proximal end and configured to allow a user to maintain and release tension on a suture thread, the suture thread being configured to allow an anchor loop structure to be formed in the distal end of the elongate tube.

3. The catheter of claim 1, wherein the first radiopaque marker comprises a marker band formed of a polymeric material.

4. The catheter of claim 3, wherein the marker band is configured to be slid over the elongate tube.

5. The catheter of claim 1, wherein the at least one drainage bore comprises a first drainage bore and wherein the first radiopaque marker marks the location of the first drainage bore and wherein the first drainage bore is the most proximally positioned drainage bore on the elongate tube.

6. The catheter of claim 1, wherein the catheter comprises the first radiopaque marker and a second radiopaque marker, the first radiopaque marker disposed at a proximal portion of the distal end of the elongate tube and the second radiopaque marker disposed at a distal portion of the distal end of the elongate tube.

7. The catheter of claim 6, wherein the at least one drainage bore comprises a first drainage bore and a second drainage bore and wherein the first radiopaque marker identifies a location of first drainage bore and the second marker identifies a location of the second drainage bore.

8. The catheter of claim 1, wherein the at least one drainage bore comprises a first drainage bore and wherein a first portion of the first drainage bore is formed in the radiopaque marker prior to the radiopaque marker being coupled to the elongate tube.

9. The catheter of claim 8, wherein after the radiopaque marker has been coupled to the elongate tube, the first portion of the first drainage bore in the radiopaque marker forms a contiguous aperture with a portion of the first drainage bore in the elongate tube.

10. The catheter of claim 1, wherein the at least one drainage bore is formed in the radiopaque marker after the radiopaque marker has been coupled to the elongate tube.

11. The catheter of claim 10, wherein the at least one drainage bore is formed in the elongate tube at the same time the at least one drainage bore is formed in the radiopaque marker, such that the at least one drainage bore is in fluid communication with the lumen of the elongate tube.

12. The catheter of claim 1, wherein the first radiopaque marker comprises a cylindrical band with a lumen and two opposing open ends, wherein the first radiopaque marker is configured to be placed circumferentially around at least a portion of the elongate tube distal end.

13. The catheter of claim 12, wherein a longitudinal width of the first radiopaque marker comprises a width within a range of from about 3 cm to about 6 cm.

14. The catheter of claim 13, wherein the cylindrical marker band comprises a circular cylinder.

15. The catheter of claim 1, wherein the first radiopaque marker comprises a conical shape.

16. A catheter tube having a radiopaque marker configured to allow a practitioner to identify a location of a drainage bore of the catheter tube positioned within a patient and the location is identified using a radiographic technique, the catheter tube comprising: an elongate tube consisting of a single layer, the elongate tube having a proximal end, a distal end and a lumen extending a length thereof, the distal end of the elongate tube adapted to be advanced to a desired position within a patient; at least one drainage bore positioned within the distal end of the elongate tube, the at least one drainage bore adapted to allow passage of fluid to or from the lumen of the elongate tube and the desired position within the patient; and a radiopaque marker comprising an elastomeric material configured to allow the radiopaque marker to be heat fused to an outside surface of the distal end of the elongate tube such that the radiopaque marker does not extend radially from an adjacent outside diameter of the elongate tube and such that the radiopaque marker is configured to contact a body cavity of the patient when the elongate tube is advanced to the desired position within the patient, wherein one or more radiopaque materials are provided in connection with the elastomeric material and wherein the at least one drainage bore extends through a portion of the radiopaque marker, and wherein the radiopaque marker is coupled to be heat fused to the elongate tube using a confinement tube disposed on the outside of the elongate tube and a mandrel disposed within the lumen of the elongate tube, such that an outside surface of the radiopaque marker is substantially continuous with an adjacent outside surface of the elongate tube and an inside surface of the elongate tube at the radiopaque marker is substantially smooth.

17. The catheter tube of claim 16, wherein the at least one drainage bore comprises a first drainage bore and wherein the radiopaque marker distinguishes the location of a the first drainage bore, which is a proximal most drainage bore, the first drainage bore being in fluid communication with the lumen of the elongate tube.

18. The catheter tube of claim 16, wherein the elongate tube is comprised of a Carbothane ™ material.

19. The catheter tube of claim 16, wherein the radiopaque material is distributed throughout the elastomeric material.

* * * * *

UNITED STATES PATENT AND TRADEMARK OFFICE
CERTIFICATE OF CORRECTION

PATENT NO. : 9,962,523 B2
APPLICATION NO. : 12/147933
DATED : May 8, 2018
INVENTOR(S) : Fred P. Lampropoulos et al.

Page 1 of 1

It is certified that error appears in the above-identified patent and that said Letters Patent is hereby corrected as shown below:

In the Claims

Column 16, Line 18, Claim 1 reads, ". . . distal end and lumen . . ." which should read ". . . distal end and a lumen . . ."

Column 16, Lines 30-40, Claim 1 reads, ". . . the first radiopaque marker surrounding a portion of the elongate tube such that the first radiopaque marker is configured to come into contact with body cavity of the patient, and the at least one drainage bore passes through at least a portion of the elongate tube surrounded by the first radiopaque marker . . ." which should read ". . . the first radiopaque marker to allow . . ."

Column 18, Line 24, Claim 16 reads, ". . . is coupled to be heat fused to . . ." which should read ". . . is coupled to the elongate tube, wherein the radiopaque marker is configured to be heat fused to . . ."

Signed and Sealed this
Eleventh Day of September, 2018

Andrei Iancu
*Director of the United States Patent and Trademark Office*